United States Patent
Sihto et al.

(10) Patent No.: US 9,901,579 B2
(45) Date of Patent: Feb. 27, 2018

(54) COMPOSITIONS COMPRISING PHOSPHODIESTERASE INHIBITORS FOR USE IN THE TREATMENT OF A SOLID TUMOR IN A HUMAN PATIENT

(71) Applicant: Sartar Therapeutics Ltd, Helsinki (FI)

(72) Inventors: Harri Sihto, Helsinki (FI); Olli-Pekka Pulkka, Helsinki (FI); Olli Kallioniemi, Helsinki (FI); Heikki Joensuu, Espoo (FI)

(73) Assignee: Sartar Therapeutics Ltd, Helsinki (FI)

( * ) Notice: Subject to any disclaimer, the term of this patent is extended or adjusted under 35 U.S.C. 154(b) by 0 days.

(21) Appl. No.: 15/028,947

(22) PCT Filed: Oct. 17, 2014

(86) PCT No.: PCT/FI2014/050788
§ 371 (c)(1),
(2) Date: Apr. 13, 2016

(87) PCT Pub. No.: WO2015/055898
PCT Pub. Date: Apr. 23, 2015

(65) Prior Publication Data
US 2016/0354376 A1    Dec. 8, 2016

(30) Foreign Application Priority Data

Oct. 17, 2013 (FI) .................................. 20136029

(51) Int. Cl.
| | | |
|---|---|---|
| A61K 31/519 | (2006.01) | |
| A61K 31/00 | (2006.01) | |
| A61K 31/506 | (2006.01) | |
| A61K 45/06 | (2006.01) | |

(52) U.S. Cl.
CPC .......... *A61K 31/519* (2013.01); *A61K 31/00* (2013.01); *A61K 31/506* (2013.01); *A61K 45/06* (2013.01)

(58) Field of Classification Search
CPC .................................................... A61K 31/519
See application file for complete search history.

(56) References Cited

U.S. PATENT DOCUMENTS

2011/0053968 A1    3/2011  Zhang

FOREIGN PATENT DOCUMENTS

| EP | 2384752 A1 | 11/2011 |
|---|---|---|
| WO | WO 2013063000 A1 | 5/2013 |

OTHER PUBLICATIONS

Ambrus, J.L. et al: "Effect of imidazoquinazolinones on tumor cells in the circulation", Journal of Medicine, vol. 17, Nos. 3 & 4, 1986, pp. 219-225.
Gromova, P. et al: "Kit K641E oncogene up-regulates Sprouty homolog 4 and Trophoblast glycoprotein in interstitial cells of Cajal in a murine model of gastrointestinal stromal tumours", Journal of Cellular and Molecular Medicine, vol. 13, No. 8A, Aug. 1, 2009, pp. 1536-1548.
Kumar, D. et al: "Ultra orphan drugs and diseases", Indian Journal of Pharmacology, vol. 38, No. 5, Oct. 1, 2006, p. 375.
Murata, T. et al: "Phosphodiesterase 3 as a potential target for therapy of malignant tumors in the submandibular gland", Anti-Cancer Drugs, vol. 12, No. 1, Jan. 1, 2001, pp. 79-83.
Shimizu, K. et al: "Expression and role of phosphodiesterase 3 in human squamous cell carcinoma KB cells", Anti-Cancer Drugs, vol. 13, No. 8, Sep. 1, 2002, pp. 875-880.
Tsimberidou, A. M. et al: "Anagrelide and Imatinib Mesylate Combination Therapy in Patients With Chronic Myeloproliferative Disorders", Cancer Chemotherapy and Pharmacology, vol. 52, No. 3, Sep. 1, 2003, pp. 229-234.

*Primary Examiner* — James D. Anderson
(74) *Attorney, Agent, or Firm* — Seppo Laine Oy (57) ABSTRACT

The present invention is related to a composition comprising a phosphodiesterase inhibitor, such as anagrelide or a salt thereof, for use in the treatment of a solid tumor, such as gastrointestinal stromal tumor (GIST) or a liposarcoma, which express phosphodiesterase 3 enzymes, in a human patient.

7 Claims, 3 Drawing Sheets

COMPOSITIONS COMPRISING PHOSPHODIESTERASE INHIBITORS FOR USE IN THE TREATMENT OF A SOLID TUMOR IN A HUMAN PATIENT

FIELD OF THE INVENTION

The field of the invention relates to cancer biology. The present invention further relates to compositions and multi-drug combinations for use in the treatment of cancer.

BACKGROUND OF THE INVENTION

Approximately 1% of all human cancers are soft tissue sarcomas, which consists of more than 50 different tumor types. Soft tissue sarcomas are often malignant up to 50% of them recur or metastasize after the manifestation (Wibmer, C. 2010). Liposarcoma is the second common soft tissues sarcoma type, and depending on liposarcoma subtype, such as de-differentiated liposarcomas, it might present very aggressive disease course (Dalai, K. M. 2006). At the moment, surgical removal of tumor and radiotherapy are used to treat local disease. Chemotherapy is included in treatments in metastatic disease but responses are rarely achieved (D'Angelo, S. P. 2014).

Gastrointestinal stromal tumor (GIST) is the most common mesenchymal tumor of the gastrointestinal tract (GI) and it has been proposed to arise from progenitor cells of the interstitial cells of Cajal (Sircar, K. 1999). Strong expression of the KIT receptor tyrosine kinase (RTK) is typical for GISTs and about 80% of these tumors have a gain-of-function mutation in the KIT proto-oncogene (Hirota, S. 1998). Many GISTs lacking KIT mutation have activating mutations in the platelet-derived growth factor receptor α (PDGFRA) (Heinrich, M. C. 2003). PDGFRA is structurally related to KIT and both of these receptors belong to the same RTK family (Yarden, Y. 1987). Imatinib mesylate, a kinase inhibitor, has been known to significantly inhibit GISTs, presumably through inhibition of the KIT and PDGFRA (Heinrich, M. C. 2003). Other effective kinase inhibitors, used for the treatment of GIST, are multikinase inhibitors sunitinib and regorafenib that are used for the treatment of patients that imatinib has no effect or who have ceased to respond to imatinib (Demetri, G. D. 2006; Demetri, G. D. 2013). Some of GISTs do not respond for kinase inhibitors or they develop a resistance over time, so it is necessary to find new drug targets for GIST patients (Heinrich, M. C. 2006; Maleddu, A. 2009).

Immunohistochemical markers are crucial to the diagnostic of GIST. CD117 antibody which is targeted against an antigen in the KIT receptor is the most traditional diagnostic marker for GIST (Kindblom, L. G. 1998). High level of KIT expression is typical for GISTs which commonly harbor a KIT gene mutation in exon 9, 11, 13, or 17 (Heinrich, M. C. 2002). One of the most sensitive markers of GISTs is anoctamin 1 (ANO1; also known as DOG1) and it is considered to be even more specific marker of GIST than KIT (West, R. B., 2004; Espinosa, I. 2008; Liegl, B. 2009). Protein kinase C theta (PKCθ) is presented in most GISTs and is suggested as a useful GIST marker (Duensing, A. 2004). PKCθ specificity for GIST is however relatively low (Novelli, M. 2010). Another marker used to evaluate GISTs is the hematopoietic progenitor cell antigen CD34, whereas smooth muscle antigens, such as smooth muscle actin, desmin, embryonic myosin and heavy caldesmon are not often expressed in GISTs (Miettinen, M. 1995; Miettinen, M. 2006).

Phosphodiesterases (PDEs) selectively catalyse the hydrolysis of the 3'-phosphoester bond of the 3',5'-purine ribose cyclic monophosphates cAMP and cGMP. PDEs regulate the cellular levels, localisation and signalling of cAMP and/or cGMP by controlling their degradation (Beavo, J. A. 1995). There is totally 11 different PDE families and many of these families have multiple transcription variants (Conti, M. 2007). PDE3 family includes two proteins, PDE3A and PDE3B, which show structural similarity (Degerman, E. 1997). PDE3A is abundant in cardiac myocytes, vascular smooth muscle cells and platelets (Shakur, Y. 2001). PDE3 inhibitors have been reported to enhance myocardial contractility and induce vascular and airway smooth-muscle relaxation (Halpin, D. M. 2008). Different PDE3 inhibitors have been used to treat heart failure and intermittent claudication (Dawson, D. L. 1998; Liu, Y. 2001). PDE3B is expressed in pancreatic beta-cells, hepatocytes and adipocytes, in which it regulates metabolic processes such as insulin secretion of beta-cells, glycogenolysis of liver cells and lipolysis in adipocytes (Resjö, S. 1999). In obese diabetic mice, PDE3 inhibitor cilotazol has been showed to improve glucose intolerance and insulin resistance by suppressing macrophage secreted TNFα-induced inflammation in adipose tissue (Wada, T. 2013).

PDE3A is phosphorylated and activated by AKT in mammalian oocyte maturation. (Han, S. J. 2006). Similarly, PDE3B is showed to be phosphorylated and activated by AKT after insulin stimulation in adipocytes (Degerman, E. 1998). The phosphatidyl-inositol-3-kinase (PI3-K)/AKT pathway is also activated by mutated KIT and PDGFRA receptors in GISTs (Duensing, A. 2004). In platelets PKC is involved in regulation of PDE3A activity (Hunter, R. W. 2009). PDE3A has been shown to be expressed in gastric smooth muscle, where PDE3A is phosphorylated by protein kinase A (Murthy, K. S. 2002). In addition, PDE3A showed strong expression in the gastric antrum of a murine model of GIST ($KIT^{K641E}$ mouse), and was associated with the gene expression profile of interstitial cells of Cajal (Gromova, P. 2009).

Anagrelide hydrochloride is a molecule which targets PDE3 enzymes and is able to lower the amounts of platelets. It has been used in patients with myeloproliferative disorders and especially for the treatment of essential thrombocytosis (Fruchtman, S. M. 2005; Harrison, C. N. 2005). Anagrelide hydrochloride inhibits the cyclic AMP phosphodiesterase activity in platelets, which further elevates the cAMP levels in these cells (Gillespie, E. 1988; Seiler, S. 1987).

In the present invention, we'll demonstrate that PDE3A and PDE3B are specific markers for GIST. PDE3 proteins are also expressed often in liposarcomas and less frequently in other cancer types. Inhibition of PDE3 activity with anagrelide hydrochloride halts cell proliferation in GIST cell lines and significantly decreases cell proliferation in liposarcomas cell line. When anagrelide hydrochloride, a PDE3 specific inhibitor, was used in combination with imatinib mesylate in GIST cell lines, synergistic effect could be seen. The GIST cells were more apoptotic and cell proliferation decreased more than using either of the drugs alone. Our findings here show that PDE3A and PDE3B can be considered new immunomarkers and drug targets, and PDE3 inhibitor anagrelide hydrochloride has strong therapeutic potential for the treatment of PDE3 expressing solid tumors.

SUMMARY OF THE INVENTION

One of the objects of the present invention is to provide a composition comprising anagrelide or a salt thereof or a other phosphodiesterase 3 inhibitor for use in the treatment of a PDE3A and/or PDE3B expressing solid tumor in a human patient.

A method for detection of a malignancy associated with expression of PDE3 proteins, in a test sample, is also provided, the method comprising: (a) contacting the sample with an antibody specifically binding to PDE3A or PDE3B enzyme, wherein said sample is taken from a tissue suspected to contain PDE3A and/or PDE3B expressing tumor; (b) incubating the specimen and the antibody for a duration and under conditions that are sufficient for the formation of immunocomplexes; (c) detecting the presence or absence of immunocomplex formation between the antigen and the antibody, and (d) determining the presence or absence of the malignancy, wherein presence of immunocomplex formation is indicative of malignancy.

Further, the present invention provides a method for detecting and analyzing whether a patient suffering from PDE3A and/or PDE3B expressing tumor, is responsive or non-responsive to the treatment with an inhibitor of phosphodiesterase 3 enzymes, the method comprising the steps of:
  determining in a tumor sample obtained from said patient the expression level of PDE3A and PDE3B enzymes, and
  selecting said patient for the treatment with said inhibitor of phosphodiesterase 3 enzymes,
if the tumor sample of said patient displays high expression of phosphodiesterase 3A and/or 3B enzymes compared to healthy control tissue sample.

BRIEF DESCRIPTION OF THE DRAWINGS

FIG. 1 discloses effects of PDE3 inhibitors, anagrelide hydrochloride, amrinone, milrinone and cilotazol on GIST and liposarcoma cell proliferation in comparison with DMSO treatment (A) GIST882 (B) GIST48 (C) LPS141. DMSO was used as a negative control for drug responses. Nilotinib was used as a positive control for drug responses in GIST cell lines.

FIG. 2 discloses effects of anagrelide hydrochloride, imatinib and combination of anagrelide hydrochloride and imatinib on GIST cell proliferation. (A) GIST882 (B) GIST48. DMSO was used as a negative control for drug responses.

DETAILED DESCRIPTION OF THE PRESENT INVENTION

Anagrelide's chemical name is 6,7-dichloro-1,5-dihydroimidazo[2,1-b]quinazolin-2(3H)-one. However, the term "anagrelide" is used herein so that it covers nontoxic pharmaceutically acceptable acid addition salts of anagrelide. Thus, the term anagrelide encompasses all of such salts as well as the parent compound. Suitable salts of anagrelide include the hydrochloride, hydrobromide, hydroiodide, (lower)alkylsulfates, (lower)alkyl- and arylsulfonates, phosphate, sulfate, maleate, fumarate, succinate, tartrate and citrate salts. Anagrelide hydrochloride is a particularly preferred acid addition salt in this invention. Preparation of anagrelide is disclosed, e.g., in U.S. Pat. No. 5,391,737.

The majority of the gastrointestinal stromal tumors (GIST) are characterized by the activating mutations in the receptor tyrosine kinase genes KIT or PDGFRA. Inhibitors of KIT and PDGFRA receptors are found to be effective in the clinic, but some tumors are unresponsive or develop resistance to the therapies upon treatment. In the present invention, we investigated the role of phosphodiesterase 3A and phosphodiesterase 3B (PDE3A, Gene ID: 5139; PDE3B, Gene ID: 5140) in GIST and other PDE3 enzymes expressing tumors as a potential new therapy target.

Figure 1A:
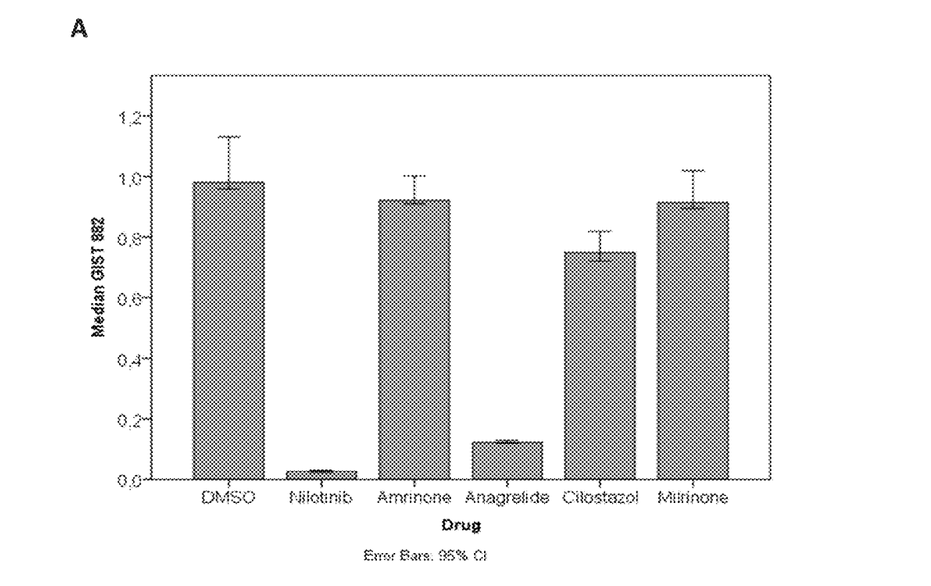
Figure 1B:
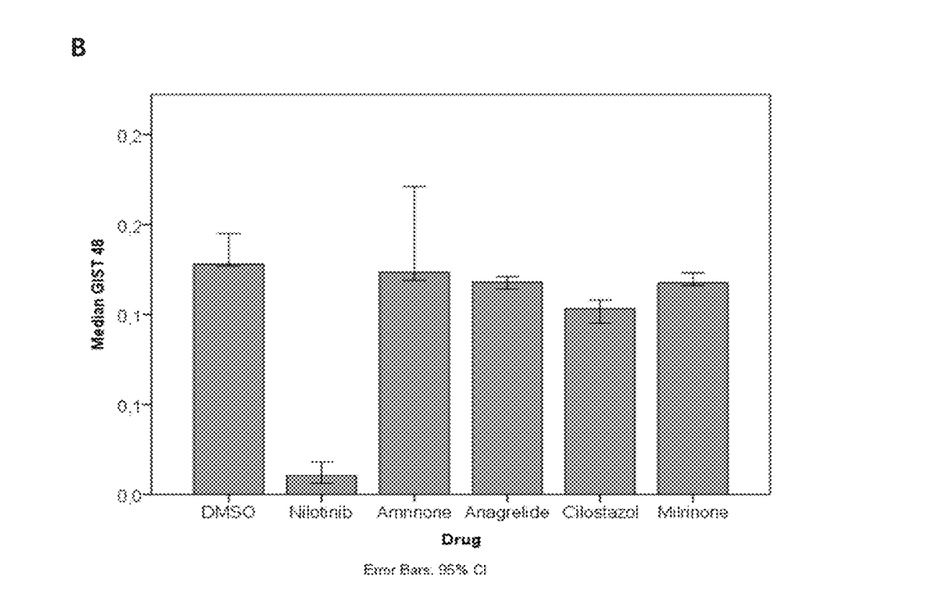
Figure 1C:
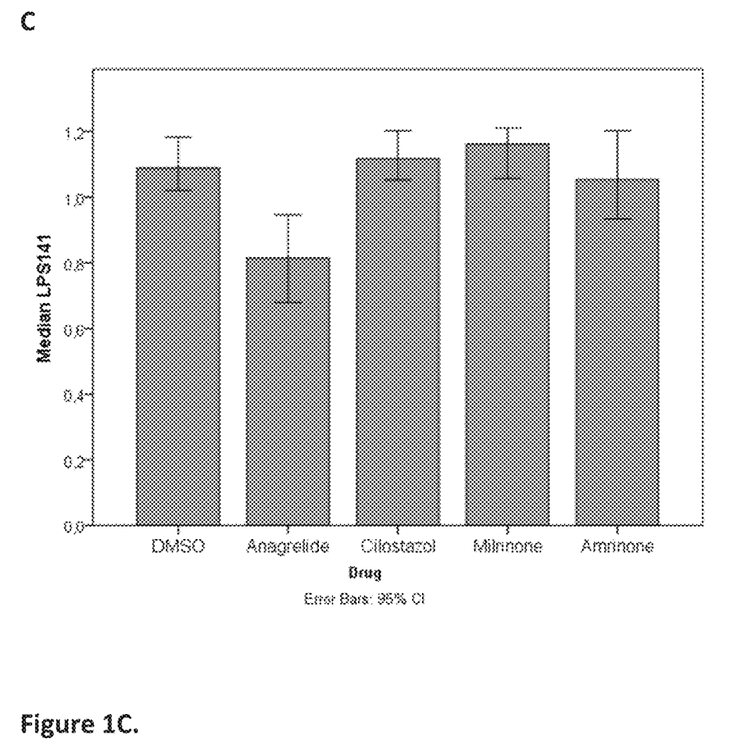

According to the GeneSapiens database, PDE3A gene showed abnormally high expression in GISTs, leiomyosarcomas and liposarcomas, and infrequently in other tumor types in comparison with other cancer types. PDE3B expression was abnormal high in liposarcomas and GISTs and rarely in other tumor types. PDE3A and PDE3B expression in cancer was further investigated in 805 human tumor tissue samples consisting of 36 different cancer types using immunohistochemistry. Specificity of immunohistochemistry was confirmed by measuring the expression levels of PDE3A and PDE3B in tumor tissues using quantitative PCR. Importance of PDE3 enzymes for tumor cell proliferation and survival was investigated in human liposarcomas cell line LPS141, and in human GIST48 and GIST882 cell lines by inhibiting activity of PDE3 enzymes with several inhibitors. The majority of GISTs (93%) expressed PDE3A (Table 1), whereas their expression was rare in other tumor types. Also PDE3B expression was most commonly found in GISTs (66%). As showed in the Examples, anagrelide hydrochloride inhibited effectively GIST and liposarcoma cell proliferation (FIG. 1). It also increased apoptosis of the GIST cells. In addition, anagrelide hydrochloride shows synergistic antitumorigenic effect in the GIST cell lines when administered with imatinib mesylate, which is a KIT and PDGFRA inhibitor.

Anagrelide hydrochloride is thus able to induce cell death and halt cell proliferation in human PDE3 proteins expressing cell lines. In addition, in a combination with imatinib mesylate, a drug used clinically in the treatment of GIST, anagrelide induces higher level cell death in GIST cell lines than either drug alone. Therefore, anagrelide and salts thereof are novel drugs to treat GIST patients. Anagrelide might be effective also in those patients whose tumor express PDE3A and/or PDE3B but does not respond or has evolved resistance to tyrosine kinase inhibitors. This is the first time when anagrelide is shown to be effective against a solid human tumor.

Accordingly, the present invention is directed to a composition comprising anagrelide for use in the treatment of a PDE3A and/or PDE3B expressing solid tumor in a human patient. Preferably, said solid tumor is gastrointestinal stromal tumor (GIST), liposarcoma or other tumor that expresses PDE3A and/or PDE3B. It is thus realized in this invention that anagrelide can be used to treat solid tumors detected to comprise cells displaying high expression of phosphodiesterase 3A (PDE3A) or phosphodiesterase 3B (PDE3B) enzyme mRNA or protein when the expression level is compared to healthy control tissue. The term "solid tumor" refers herein to an abnormal mass of tissue as a result of abnormal growth or division of cells, i.e. a neoplasm.

The most preferred composition comprises anagrelide hydrochloride. In other preferred embodiments of the invention, other salts of anagrelide can be used when formulating the composition of the invention.

The present invention is also directed to compositions for multi-drug therapies. A multi-drug composition of the present invention comprises anagrelide and imatinib or imatinib mesylate. In a multi-drug embodiment of the present invention, the composition comprising anagrelide can also be administered to a cancer patient, simultaneously or sequentially, in combination with a composition comprising imatinib or imatinib mesylate. Also other KIT and PDGFR targeting tyrosine kinase inhibitors than imatinib and imatinib mesylate, such as nilotinib, sunitinib, masitinib, dovitinib, ponatinib, pazopanib, sorafenib, dasatinib, crenolanib and regorafenib, are preferred for use in the multi-drug compositions of the present invention.

The composition comprising a phosphodiesterase inhibitor, such as anagrelide, may contain a pharmaceutically acceptable buffer, carrier or adjuvant, and may be administered orally or parenterally. The present invention thus provides pharmaceutical compositions comprising anagrelide, with pharmaceutically acceptable buffer, carrier or adjuvant. In a multi-drug embodiment, said pharmaceutical composition further comprises a tyrosine kinase inhibitor, such as imatinib or imatinib mesylate. The phrase "pharmaceutically acceptable" refers herein to compositions that are physiologically tolerable and do not typically produce an allergic or similar reaction, when administered to a patient. Said pharmaceutical composition may also be formulated for sustained-release, delayed-release, or timed-release, or said pharmaceutical composition is a blend of sustained-release and immediate-release formulations.

The composition or the pharmaceutical composition may be administered orally in the form of a solid product such as a tablet, a granule, a powder, or a capsule. For the preparation of such a solid product, the phosphodiesterase inhibitor, such as anagrelide, may be combined with an appropriate additive, such as an excipient (e.g., lactose, mannitol, cornstarch, or crystalline cellulose), a binder (e.g., a cellulose derivative, acacia gum, or gelatin), a disintegrant (e.g., carboxymethylcellulose calcium), or a lubricant (e.g., talc or magnesium stearate).

Such a solid product may be prepared into a controlled-release product by use of a coating base material such as hydroxymethylcellulose phthalate, hydroxypropylmethylcellulose acetate succinate, cellulose acetate phthalate, or methacrylate copolymer. The composition as defined in the claims may also be prepared into a liquid product such as a solution, a suspension, or an emulsion.

The composition comprising a phosphodiesterase inhibitor, such as anagrelide, may be administered parenterally in the form of an injection. For the preparation of an injection, the composition may be combined with, for example, water, ethanol, glycerin, or a conventionally employed surfactant. The composition may also be prepared into a suppository by use of an appropriate base material.

The composition comprising a phosphodiesterase inhibitor, such as anagrelide, may be administered in combination with an antitumor agent employed in multi-drug combination therapy or with radiation therapy, in which said composition and the antitumor agent may be administered simultaneously or separately at the same frequency of dosage or different frequencies through the same administration method or different administration methods. Thus, the phosphodiesterase inhibitor may be employed in combination with multi-drug combination therapy or with radiation therapy for treating cancer patients. The preferred antitumor agent in multi-drug combination is a tyrosine kinase inhibitor, such as imatinib or imatinib mesylate. The preparation of 4-(4-methylpiperazin-1-ylmethyl)-N-[4-methyl-3-(4-(pyridin-3-yl)pyrimidin--2-ylamino)phenyl]-benzamide, also known as imatinib, and its use, especially as an anti-tumour agent, are described in EP 0 564 409. 4-(4-Methyl-piperazin-1-ylmethyl)-N-[4-methyl-3-(4-(pyridin-3-yl)pyrimidin--2-ylamino)phenyl]-benzamide mesylate, also known as imatinib mesylate or STI571 and its pharmaceutical use are described in U.S. Pat. No. 6,894,051.

The preferred single dose for humans of anagrelide is 0.025-2.5 mg, preferably 0.1-1.0 mg, most preferably 0.5 mg. Daily doses of about 100-1000 mg, preferably 300-800 mg, of imatinib or imatinib mesylate are preferred. However, the optimal interval and amount of doses can be determined empirically and is within the skill of the art.

The present invention also provides a composition comprising a phosphodiesterase inhibitor for use in the treatment of phosphodiesterase 3A and/or phosphodiestarase 3B expressing tumors in a human patient (the composition of this embodiment may also be a pharmaceutical composition comprising further ingredients as defined above). Preferably, said phosphodiesterase inhibitor is an inhibitor of phosphodiesterase 3 enzymes. Said phosphodiesterase inhibitor can be selected from the group consisting of inhibitors such as anagrelide, milrinone, amrinone and cilostazol. Most preferably, said phosphodiesterase inhibitor is anagrelide hydrochloride. This embodiment of the present invention is also directed to compositions for multi-drug therapies. A multi-drug composition of the present invention comprises a phosphodiesterase inhibitor and a tyrosine kinase inhibitor selected from the group consisting of inhibitors such as imatinib, imatinib mesylate, nilotinib, sunitinib, masitinib, dovitinib, ponatinib, pazopanib, sorafenib, dasatinib, crenolanib, vatalanib and regorafenib. In a multi-drug embodiment of the present invention, the composition comprising a phosphodiesterase inhibitor can also be administered to a cancer patient, simultaneously or sequentially, in combination with a composition comprising a tyrosine kinase inhibitor, preferably imatinib or imatinib mesylate.

The present invention is disclosing a further medical indication for anagrelide and other phosphodiesterase 3 inhibitors. Therefore, the present invention also claims the use of anagrelide or a salt thereof for the manufacture of a medicament for the treatment of a solid tumor in a human patient. The present invention is further directed to a use of a phosphodiesterase inhibitor for the manufacture of a medicament for the treatment of gastrointestinal stromal tumor, GIST, liposarcomas and other PDE3 proteins expressing tumors.

The present invention also teaches method for treatment of a phosphodiesterase 3 proteins expressing solid tumor in a human patient, wherein a pharmaceutically effective amount of the composition comprising anagrelide or a salt thereof is administered to a patient in need of such treatment. In another embodiment, the invention teaches a method for treatment of PDE3A and/or PDE3B expressing tumors in a human patient, wherein a pharmaceutically effective amount of the composition comprising a phosphodiesterase inhibitor is administered to a patient in need of such treatment. The phrase "pharmaceutically effective amount" is used herein to mean an amount sufficient to suppress to some beneficial degree, preferably to reduce by at least about 5 percent, more preferably by at least 30 percent, most preferably by at least 50 percent, the development of tumours in human, in particular PDE3 enzymes expressing tumors such as GIST and liposarcoma.

In a further embodiment, the present invention provides a method for detection of a malignancy associated with PDE3 enzymes expressing tumors, in a test sample, the method comprising the steps of: (a) contacting the sample with an antibody specifically binding to PDE3A or PDE3B enzyme, wherein said sample is taken from a tissue suspected to contain gastrointestinal stromal tumor, GIST, liposarcoma or other PDE3A and/or PDE3B expressing tumor; (b) incubating the specimen and the antibody for a duration and under conditions that are sufficient for the formation of immuno-complexes; (c) detecting the presence or absence of immuno-complex formation between the antigen and the antibody, and (d) determining the presence or absence of the malignancy, wherein presence of immunocomplex formation is indicative of malignancy.

The detection of protein antigens, such as enzymes, is within the skill of the art, see Examples below and, e.g., U.S. Pat. No. 8,449,885.

In another further embodiment, the present invention provides a method for detecting and analyzing whether a patient suffering from PDE3A and/or PDE3B expressing tumor, is responsive or non-responsive to the treatment with an inhibitor of phosphodiesterase 3 enzyme, the method comprising the steps of:
  determining in a tumor sample obtained from said patient the expression level of PDE3A and/or PDE3B enzymes, and
  selecting said patient for the treatment with said inhibitor of phosphodiesterase 3 enzymes,
if the tumor sample of said patient displays high expression of phosphodiesterase 3A and/or phoshodiesterase 3B enzymes compared to a control tissue sample consisting of histologically normal tissue.

The expression level of PDE3A and/or PDE3B enzymes can be determined as in the Examples below or, e.g., as in U.S. Pat. No. 8,546,552.

It is also clear that a method comprising the steps of determining the expression level of PDE3A and/or PDE3B mRNAs, e.g. by PCR methods, in a tissue sample obtained from a patient suspected to suffer from a solid tumor, such as GIST or liposarcomas or other PDE3A and/or PDE3B expressing tumor, and comparing the detected level to the expression level in a corresponding healthy sample, can be used to detect malignant cells in the sample, wherein presence of high expression level of PDE3A and/or PDE3B is indicative of malignancy of the sample.

The publications and other materials used herein to illuminate the background of the invention, and in particular, to provide additional details with respect to its practice, are incorporated herein by reference. The present invention is further described in the following Examples, which are not intended to limit the scope of the invention.

EXAMPLES

Materials and Methods
Tissue Material
  Formalin-fixed, paraffin embedded tumor tissue samples were retrieved and identified. Approval to use and analyze the tissue samples was provided by the National Authority for Medico legal Affairs of Finland and the Institutional Review Board. In total, 36 histologic cancer types and over 700 tumors were analyzed in the study, including over 200 GISTs.
GeneSapiens Database
  The GeneSapiens database (http://ist.genesapiens.org/) includes gene expression data from 9783 tissue samples consisting of both histologically normal human tissue samples and cancer tissue samples (Kilpinen, S. 2008).
Immunohistochemistry and Tissue Microarray
  Formalin-fixed paraffin-embedded tissue samples were analyzed for PDE3A and PDE3B expression. Five-micrometre sections were cut onto SuperFrost™+ slides (Menzel-Glaser). The sections were deparaffinised in xylene and hydrated in a graded series of alcohol. 1% hydrogen peroxide was used to block endogenous peroxidase activity. Antigen retrieval for immunohistochemistry was carried out in sodium citrate (0.01 mol/L, pH 6.0) in an autoclave (at 120° C. for 2 minutes). The primary antibody used for PDE3A immunostaining was a polyclonal rabbit Anti-PDE3A antibody (dilution 1:100; SIGMA, St. Louis, Mo., USA) and the primary antibody used for PDE3B immunostaining was a polyclonal rabbit Anti-PDE3B antibody (dilution 1:20; SIGMA, St. Louis, Mo., USA). The primary antibody was diluted in a PowerVision preantibody blocking solution and incubated 30 minutes at room temperature. Primary antibody binding was detected by using a BrightVision+ Histostaining kit (Immunologic BV, Duiven, The Netherlands) following the manufacturer's instructions. Expression of the studied protein in tumor cells was scored as follows: negative (less than 10% of tumor cells stained) or positive [weak (+), moderate (++) or strong (+++) staining intensity].
Quantification of PDE3A and PDE3B Gene Expression
  The mRNA was extracted from the formalin-fixed paraffin-embedded tissue blocks with the use of the High Pure RNA Paraffin kit (Roche Diagnostics GmbH, Mannheim, Germany) or from the GIST cell lines with the use of the High Pure RNA Isolation Kit (Roche Diagnostics GmbH). The mRNA was reverse transcribed to cDNA with the SuperScript® VILO™ cDNA Synthesis Kit (Invitrogen, Carlsbad, Calif., USA) according to the manufacturer's instructions.
  PDE3A and PDE3B expression levels were quantified from seven GIST, 32 leiomyosarcoma tissue samples and samples from GIST cell lines by performing real-time PCR with hydrolysis probes (i.e., hybridization probes labeled with a reporter dye and a quenching dye) in a LightCycler 480 instrument (Roche Diagnostics GmbH). cDNA (50 ng) was amplified in a 20 µL PCR mixture using LightCycler 480 Probes Master reagents (Roche Diagnostics GmbH) and the fluorescein-labeled locked nucleic acid (LNA) hydrolysis probes (Probe 79 for PDE3A and Probe 10 for PDE3B) or the LightCycler® Yellow 555-labeled LNA hydrolysis probes (Probe TBP for PDE3A and Probe G6PD for PDE3B) from a Universal ProbeLibrary Set (Roche Diagnostics GmbH). The PCR mixture contained 1× PCR buffer, 100 nmol/L of probe, and 200 nmol/L of each primer specific for the PDE3A coding region (forward: 5'-AAAGACAAGCTTGCTATTCCAAA-3', SEQ ID NO:1; reverse: 5'-GTGGAAGAAACTCGTCTCAACA-3', SEQ ID NO:2) or for the PDE3B coding region (forward: 5'-AACAATGGTATAAGCCTCATTATCAA-3', SEQ ID NO:5; reverse: 5'-CGAGCCTCATTTAGCACTGA-3', SEQ ID NO:6) or for TBP as a reference DNA (forward: 5'-TGAATCTTGGTTGTAAACTTGACC-3', SEQ ID NO:3; reverse: 5'-CTCATGATTACCGCAGCAAA-3', SEQ ID NO:4) or G6PD as a reference DNA (forward: 5'-GAGCCAGATGCACTTCGTG-3', SEQ ID NO:7; reverse: 5'-GGGCTTCTCCAGCTCAATC-3', SEQ ID NO:8). The primers and the probes were designed using the ProbeFinder program at the Assay Design Center of Universal ProbeLibrary (Roche Diagnostics GmbH).
  The cycling parameters were an initial denaturation at 95° C. for 10 minutes, followed by 60 cycles with denaturation at 95° C. for 15 seconds, annealing at 60° C. for 45 seconds and elongation at 72° C. for 45 seconds.
Cell Lines
  GIST882 is a primary human GIST cell line with a homozygous missense mutation in KIT exon 13, encoding a K642E mutant KIT oncoprotein (Tuveson, D. A. 2001). GIST48 is a GIST cell line produced from a GIST that progressed after initial clinical response during imatinib therapy. GIST48 has a primary exon 11 missense mutation and a secondary exon 17 missense mutation (Bauer, S. 2006). LPS141 is a liposarcoma cell line that is established from patient derived de-differentiated liposarcoma (Snyder, E. L. 2009). The cell lines were cultured in a RPMI 1640 medium (GIBCO, California USA) supplemented with 20% fetal bovine serum (FBS) and 2% penicillin/streptomycin.

PDE3 and Kinase Inhibitors, a TUNEL Assay

Four different PDE3-inhibitors were used to block the activity of PDE3 enzymes and two kinase-inhibitors to block the activity of KIT and PDGFRA. Cilostazol, milrinone and amrinone were purchased from Sigma (St Louis, Mo., USA) and anagrelide hydrochloride was purchased from Tocris Bioscience (Bristol, UK). Imatinib and nilotinib (KIT specific inhibitors, Novartis) were purchased from Cayman Chemical Company (Ann Arbor, Mich., USA). Imatinib was reconstituted in water. All other inhibitors were reconstituted in DMSO. In a preliminary analysis, multiple drug concentrations (from 0 to 100 µmol/L) were used to identify effective PDE3 inhibitor doses in the GIST cell lines. Effects on proliferation were analysed using xCELLigence System and the RTCA DP instrument (Acea Biosciences, San Diego, Calif., USA). The final inhibitor concentrations used in the further analyses were 0.5 µmol/L for imatinib and nilotinib, and 10 µmol/L for PDE3 inhibitors. Cell progression to apoptosis after anagrelide hydrochloride treatment was analysed in eight duplicate wells with a Click-iT TUNEL Alexa Fluor 488 Imaging Assay (Invitrogen, Carlsbad, Calif., USA) according to the manufacturer's instructions. Progression to apoptosis was measured after 48 hours and after 96 hours of drug treatments.

Cell Proliferation

Cell proliferation was examined by the MTT assay (Roche Diagnostics, Indianapolis, Ind., USA) and the xCELLigence System using the RTCA DP instrument (Acea Biosciences). For the MTT assay, GIST882 cells were plated at a density of $1.5 \times 10^4$ cells/well, GIST48 cells were plated at a density of $2.0 \times 10^4$ cells/well and LPS141 cells were plated at a density of $5.0 \times 10^3$ cells/well. At the end of the incubation, cell proliferation was analyzed from eight duplicate wells by adding 10 µL of the MTT reagent into each well and incubating at 37° C. for four hour. The plates were read with a Multiscan EX Microplate photometer (Thermo Scientific, Rockford, Ill., USA) at the wavelength of 540 nm. For the xCELLigence proliferation assay GIST48 and GIST882 cells were plated at a density of $2.5 \times 10^4$ cells/well. Before plating GIST882 cells, the wells were thin coated with Collagen I Rat Tail (Invitrogen, Carlsbad, Calif., USA) according to the manufacturer's instructions using 7.5 µg/mL final collagen concentration.

Statistical Analysis

Differences between groups were analysed using the Kruskal-Wallis's analysis of variance or the Mann-Whitney U-test. The P-values are two-sided.

Results

GeneSapiens Database

Phosphodiesterase 3A and phosphodiesterase 3B enzyme mRNAs were identified to be expressed strongly in GIST and liposarcoma as compared with other tumor types using GeneSapiens database (http://ist.genesapiens.org/).

PDE3A and PDE3B Expression in Cancer Tissues

PDE3 expression in cancer tissue was investigated in 805 patient samples by using tumor tissue microarrays. PDE3A expression was detected in 93% of GISTs and in 33% of liposarcomas, and infrequently in other tumor types (Table 1). Intensity of PDE3A immunostaining was moderate or strong in the majority of the GISTs. Altogether less than 11% of tumors other than GIST showed PDE3A expression. PDE3B expression was detected in 66% of GISTs and in 19% of liposarcomas. 4% of other tumors than GIST showed PDE3B expression. The investigated tumors besides GIST included carcinomas of the breast, prostate, ovary, colon, uterus, pancreas, liver, bladder, kidney, lung and the gall ducts; and gliomas, germ cell tumors, sarcomas, melanomas, schwannomas, menigeomas, lymphoepitheliomas, neuroblastomas and oncocytomas.

Specificity of PDE3 immunostainings was verified by measuring PDE3A and PDE3B mRNA expression with qPCR. PDE3A and PDE3B mRNA was expressed abundantly in all seven GISTs (100%) but only in a minority of leiomyosarcoma tissue samples, verifying the immunohistochemical staining results. Protein and mRNA expressions showed statistically significant correlation (P<0.001).

PDE3 Inhibitor Treatments

Figure 2A:
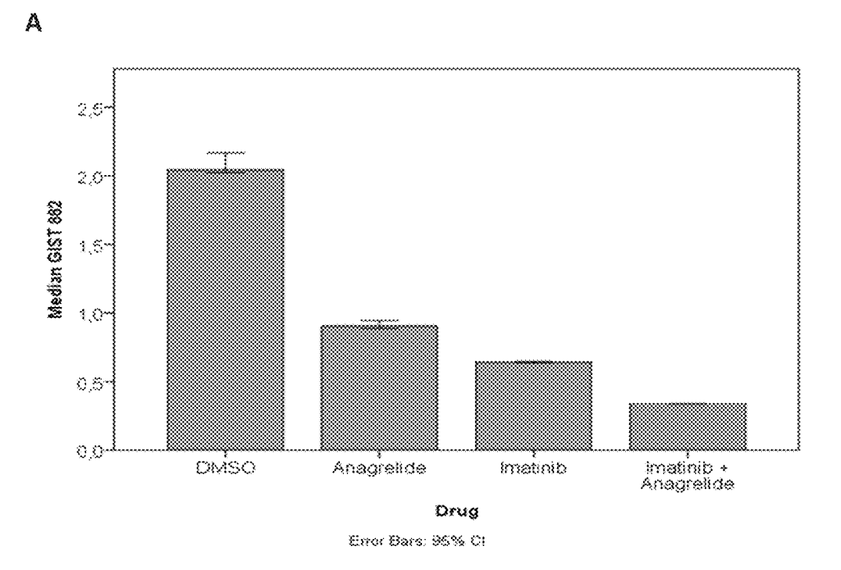
Figure 2B:
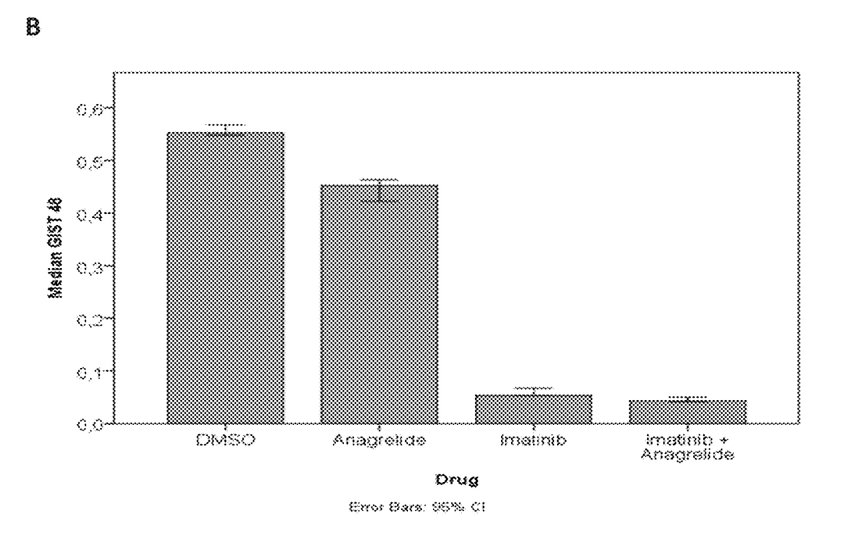

In an analysis performed by using xCELLigence System and the RTCA DP instrument (Acea Biosciences), 10 µmol/L or higher concentration of anagrelide and amrinone showed some anti-proliferative effect on GIST cell cultures, whereas cilostazol and milrinone did not influence cell proliferation. To examine more closely the effects of PDE3 inhibitors on LPS141, GIST882 and GIST48 cell lines, the cells were cultured at the 10 µmol/L final concentrations of PDE3 inhibitors for 96 hours, and the drug effects on proliferation were measured with MTT assay and compared to the anti-proliferative effect of nilotinib (0.5 µmol/L). Over a four day culture period, anagrelide hydrochloride turned out to be the only PDE3 inhibitor that had an effect on GIST882 and LPS141 cell growth in comparison with DMSO. None of the PDE3 inhibitors influenced significantly proliferation of GIST48 cells (FIG. 1). Next, the effect of anagrelide hydrochloride (10 µmol/L) combined with imatinib (0.5 µmol/L) treatment was investigated on the GIST cell lines. Again, during a four day culture, only the GIST882 cell line was affected, and the drug combination showed synergistic anti-proliferative effects on the cells (FIG. 2).

The effect of anagrelide hydrochloride and the combination of anagrelide hydrochloride and imatinib on tumor cell apoptosis was investigated with a TUNEL assay that detects fragmented DNA in cell nuclei. 22% of anagrelide hydrochloride-treated GIST882 cells were apoptotic after 48 hours and 47% after 96 hours. In GIST48 cells only slight DNA fragmentation was observed when the cells were treated with anagrelide hydrochloride. 48 hours after starting anagrelide hydrochloride treatment 0.6% of GIST48 cells were apoptotic, and after 96-hour culture 1%. 22% and 1% of the GIST882 cells were apoptotic after 48 and 96 hours of imatinib treatment, respectively. The apoptosis rate in GIST48 cells treated with imatinib for 48 and 96 hours, respectively, was 34% and 40%. When anagrelide hydrochloride and imatinib were used in a combination, a synergistic effect was detected in both GIST cell lines. After 48 and 96 hours 32% and 86% of GIST882 cells, and 39% and 47% of GIST48 cells, respectively, were apoptotic in the assay.

Discussion

Many GIST patients progress despite the current treatments. Imatinib mesylate, an inhibitor of several type III receptor tyrosine kinases, inhibits progression of advanced GISTs (Demetri, G. D. 2002). Most GISTs have an oncogenic mutation in KIT or PDGFRA (Hirota, S. 1998; Heinrich, M. C. 2003), which are regarded as the primary targets for imatinib therapy. Some GISTs lack of response to tyrosine kinase inhibitors or develop resistance to them, often due to secondary mutations. In the present invention we demonstrate that PDE3A and PDE3B are new potential immunomarkers and new therapeutic targets of treatment for GIST, liposarcomas and other PDE3 enzymes expressing tumors.

Based on the GeneSapiens database search, PDE3A and PDE3B mRNA expression is high in GISTs and liposarcomas when compared with other human cancer types. Similarly, in clinical tumor tissue samples most GISTs express the PDE3A and PDE3B protein, whereas its expression is found less often in other tumor types. PDE3A was expressed in the gastric antrum in a murine model of GIST ($KIT^{K641E}$ mouse),) and it is also associated with the gene expression profile of the interstitial cells of Cajal (Gromova, P. 2009), which might have same progenitor cells with GIST (Sircar, K. 1999). Therefore, PDE3A might be important for the function of both interstitial cells of Cajal and GIST cells.

Because abundant PDE3A and PDE3B expression was found mainly in GISTs, we hypothesized that expression and activity of these proteins might be crucial for GIST tumor cell survival. In consequence of PDE3 inhibition with anagrelide hydrochloride, GIST cell proliferation was blocked and tumor cells became apoptotic. Similarly, liposarcomas cell proliferation decreased due to PDE3 inhibition, indicating that PDE3A and/or PDE3B expressing tumors generally are suitable for PDE3 inhibition therapies.

PDE3A and PDE3B are enzymes that catalyzes the hydrolysis of the 3'-phosphoester bond of cAMP and cGMP, producing AMP and GMP (Beavo, J. A. 1995). Cyclic nucleotides, especially cAMP, regulate many physiological processes. One of the most important targets of cAMP is PKA, which further regulates gene expression and many physiological processes in the cells (Beavo, J. A. 2002). Addiction to the maintenance of low levels of cAMP through PDE4 hydrolysis in the appropriate subcellular locations was connected with the cell proliferation rate and survival in a chemoresistant colorectal cancer cell line (McEwan, D. G. 2007). It is possible that some tumors are addicted to PDE3 signalling and cell addiction to low cAMP levels is one of the key players in the regulation of cell survival, and pharmaclologic influence on this pathway may afford clinical benefit. Expression of other cAMP specific phosphodiesterases may compensate for a loss of PDE3A or PDE3B function during anagrelide hydrochloride treatment in cell lines. Eight phosphodiesterase enzyme families are known to regulate the activity of cAMP within cells, and the majority of cAMP hydrolysing activity stems from the PDE3 and PDE4 families (Conti, M. 2007; McEwan, D. G. 2007). Anagrelide hydrochloride potentiated the effects of imatinib in both GIST cell lines. This might be due the fact that inhibitors target different cell signalling pathways in target cells. Therefore, synergistic effects of anagrelide hydrochloride and receptor tyrosine kinase inhibitors on GIST is expected to be found also in the clinic.

Anagrelide is a potential novel method to treat PDE3 expressing tumors. It may also be an option to treat GIST patients who no longer respond to tyrosine kinase inhibitors or who have GIST with no KIT or PDGFRA gene mutation. Anagrelide is also a potential drug for combination therapy with kinase inhibitors.

In conclusion, PDE3A and PDE3B are expressed in the majority of GISTs and often in liposarcomas, but rarely in other human solid tumors. Therefore, PDE3A and PDE3B can be considered as a new biomarker for GIST and liposarcomas, and PDE3-expressing tumors can be identified for example with immunohistochemistry or nucleic acid amplification methods. PDE3-positive tumors serve as a target for PDE3 inhibitors, especially for anagrelide that is able to induce apoptosis and prevent cell proliferation of tumor cells. Anagrelide is a potential new drug to treat GISTs either alone or in a combination with other medicinal agents.

TABLE 1

Phosphodiesterase 3A and 3B protein expression in human tumor samples.

| Tumor type | No. of cases 805 | Expression % PDE3A | Expression % PDE3B |
| --- | --- | --- | --- |
| GIST | 230 | 93% | 66% |
| Liposarcoma | 42 | 33% | 19% |
| Germ cell tumors | 23 | 17% | 0% |
| Other sarcomas | 114 | 16% | 7% |
| Lung cancers | 53 | 13% | 0% |
| Brain tumors | 94 | 12% | 1% |
| Other cancers | 112 | 9% | 3% |
| Kidney cancers | 53 | 0% | 2% |
| Breast cancers | 84 | 0% | 0% |

REFERENCES

Andersson, J., Bumming, P., Meis-Kindblom, J. M., Sihto, H., Nupponen, N., Joensuu, H., Oden, A., Gustaysson, B., Kindblom, L. G. and Nilsson, B. (2006). Gastrointestinal stromal tumors with KIT exon 11 deletions are associated with poor prognosis. Gastroenterology 6, 1573-1581.

Bauer, S., Yu, L. K., Demetri, G. D. and Fletcher, J. A. (2006). Heat shock protein 90 inhibition in imatinib-resistant gastrointestinal stromal tumor. Cancer Res. 18, 9153-9161.

Beavo, J. A. (1995). Cyclic nucleotide phosphodiesterases: functional implications of multiple isoforms. Physiol. Rev. 4, 725-748.

Beavo, J. A. and Brunton, L. L. (2002). Cyclic nucleotide research—still expanding after half a century. Nat. Rev. Mol. Cell Biol. 9, 710-718.

Conti, M. and Beavo, J. (2007). Biochemistry and physiology of cyclic nucleotide phosphodiesterases: essential components in cyclic nucleotide signaling. Annu. Rev. Biochem. 481-511.

D'Angelo, S. P., Tap, W. D., Schwartz, G. K. and Carvajal, R. D. (2014). Sarcoma immunotherapy: past approaches and future directions. Sarcoma 2014: 391967.

Dalal, K. M., Antonescu, C. R. and Singer, S. (2008). Diangosis and management of lipomatous tumors. J. Surg. Oncol. 97, 298-313.

Dawson, D. L., Cutler, B. S., Meissner, M. H. and Strandness, D. E., Jr. (1998). Cilostazol has beneficial effects in treatment of intermittent claudication: results from a multicenter, randomized, prospective, double-blind trial. Circulation 7, 678-686.

Degerman, E., Belfrage, P. and Manganiello, V. C. (1997). Structure, localization, and regulation of cGMP-inhibited phosphodiesterase (PDE3). J. Biol. Chem. 11, 6823-6826.

Degerman, E., Landström, T. R., Wijkander, J., Holst, L. S., Ahmad, F., Belfrage, P. and Manganiello, V. (1998). Phosphorylation and activation of hormone-sensitive adipocyte phosphodiesterase type 3B. Methods 14, 43-53.

Demetri, G. D., Reichardt, P., Kang, Y. K., Blay, J. Y., Rutkowski, P., Gelderblom, H., Hohenberger, P., Leahy, M., von Mehren, M., Joensuu, H. et al. (2013). Efficacy and safety of regorafenib for advanced gastrointestinal stromal tumours after failure of imatinib and sunitinib (GRID): an international, multicentre, randomised, placebo-controlled, phase 3 trial. Lancet 9863, 295-302.

Demetri, G. D., van Oosterom, A. T., Garrett, C. R., Blackstein, M. E., Shah, M. H., Verweij, J., McArthur, G., Judson, L R., Heinrich, M. C., Morgan, J. A. et al. (2006). Efficacy and safety of sunitinib in patients with advanced gastrointestinal stromal tumour after failure of imatinib: a randomised controlled trial. Lancet 9544, 1329-1338.

Demetri, G. D., von Mehren, M., Blanke, C. D., Van den Abbeele, A. D., Eisenberg, B., Roberts, P. J., Heinrich, M. C., Tuveson, D. A., Singer, S., Janicek, M. et al. (2002). Efficacy and safety of imatinib mesylate in advanced gastrointestinal stromal tumors. N. Engl. J. Med. 7, 472-480.

Duensing, A., Joseph, N. E., Medeiros, F., Smith, F., Hornick, J. L., Heinrich, M. C., Corless, C. L., Demetri, G. D., Fletcher, C. D. and Fletcher, J. A. (2004). Protein Kinase C theta (PKCtheta) expression and constitutive activation in gastrointestinal stromal tumors (GISTs). Cancer Res. 15, 5127-5131.

Duensing, A., Medeiros, F., McConarty, B., Joseph, N. E., Panigrahy, D., Singer, S., Fletcher, C. D., Demetri, G. D. and Fletcher, J. A. (2004). Mechanisms of oncogenic KIT signal transduction in primary gastrointestinal stromal tumors (GISTs). Oncogene 22, 3999-4006.

Espinosa, I., Lee, C. H., Kim, M. K., Rouse, B. T., Subramanian, S., Montgomery, K., Varma, S., Corless, C. L., Heinrich, M. C., Smith, K. S. et al. (2008). A novel monoclonal antibody against DOG1 is a sensitive and specific marker for gastrointestinal stromal tumors. Am. J. Surg. Pathol. 2, 210-218.

Fruchtman, S. M., Petitt, R. M., Gilbert, H. S., Fiddler, G., Lyne, A. and Anagrelide Study Group. (2005). Anagrelide: analysis of long-term efficacy, safety and leukemogenic potential in myeloproliferative disorders. Leuk. Res. 5, 481-491.

Gillespie, E. (1988). Anagrelide: a potent and selective inhibitor of platelet cyclic AMP phosphodiesterase enzyme activity. Biochem. Pharmacol. 14, 2866-2868.

Gromova, P., Ralea, S., Lefort, A., Libert, F., Rubin, B. P., Erneux, C. and Vanderwinden, J. M. (2009). Kit K641E oncogene up-regulates Sprouty homolog 4 and trophoblast glycoprotein in interstitial cells of Cajal in a murine model of gastrointestinal stromal tumours. J. Cell. Mol. Med. 8A, 1536-1548.

Halpin, D. M. (2008). ABCD of the phosphodiesterase family: interaction and differential activity in COPD. Int. J. Chron. Obstruct Pulmon Dis. 4, 543-561.

Han, S. J., Vaccari, S., Nedachi, T., Andersen, C. B., Kovacina, K. S., Roth, R. A. and Conti, M. (2006). Protein kinase B/Akt phosphorylation of PDE3A and its role in mammalian oocyte maturation. EMBO J. 24, 5716-5725.

Harrison, C. N., Campbell, P. J., Buck, G., Wheatley, K., East, C. L., Bareford, D., Wilkins, B. S., van der Walt, J. D., Reilly, J. T., Grigg, A. P. et al. (2005). Hydroxyurea compared with anagrelide in high-risk essential thrombocythemia. N. Engl. J. Med. 1, 33-45.

Heinrich, M. C., Blanke, C. D., Druker, B. J. and Corless, C. L. (2002). Inhibition of KIT tyrosine kinase activity: a novel molecular approach to the treatment of KIT-positive malignancies. J. Clin. Oncol. 6, 1692-1703.

Heinrich, M. C., Corless, C. L., Duensing, A., McGreevey, L., Chen, C. J., Joseph, N., Singer, S., Griffith, D. J., Haley, A., Town, A. et al. (2003). PDGFRA activating mutations in gastrointestinal stromal tumors. Science 5607, 708-710.

Heinrich M C, Corless C L, Blanke C D, Demetri G D, Joensuu H, Roberts P J, Eisenberg B L, von Mehren M, Fletcher C D, Sandau K, et al. (2006). Molecular correlates of imatinib resistance in gastrointestinal stromal tumors. J. Clin. Oncol. 24, 4764-4774.

Hirota, S., Isozaki, K., Moriyama, Y., Hashimoto, K., Nishida, T., Ishiguro, S., Kawano, K., Hanada, M., Kurata, A., Takeda, M. et al. (1998). Gain-of-function mutations of c-kit in human gastrointestinal stromal tumors. Science 5350, 577-580.

Hunter, R. W., Mackintosh, C. and Hers, I. (2009). Protein kinase C-mediated phosphorylation and activation of PDE3A regulate cAMP levels in human platelets. J. Biol. Chem. 18, 12339-12348.

Kilpinen, S., Autio, R., Ojala, K., Iljin, K., Bucher, E., Sara, H., Pisto, T., Saarela, M., Skotheim, R. I., Bjorkman, M. et al. (2008). Systematic bioinformatic analysis of expression levels of 17,330 human genes across 9,783 samples from 175 types of healthy and pathological tissues. Genome Biol. 9, R139-2008-9-9-r139. Epub 2008 Sep. 19.

Kindblom, L. G., Remotti, H. E., Aldenborg, F. and Meis-Kindblom, J. M. (1998). Gastrointestinal pacemaker cell tumor (GIPACT): gastrointestinal stromal tumors show phenotypic characteristics of the interstitial cells of Cajal. Am. J. Pathol. 5, 1259-1269.

Liegl, B., Hornick, J. L., Corless, C. L. and Fletcher, C. D. (2009). Monoclonal antibody DOG1.1 shows higher sensitivity than KIT in the diagnosis of gastrointestinal stromal tumors, including unusual subtypes. Am. J. Surg. Pathol. 3, 437-446.

Liu, Y., Shakur, Y., Yoshitake, M. and Kambayashi Ji, J. (2001). Cilostazol (pletal): a dual inhibitor of cyclic nucleotide phosphodiesterase type 3 and adenosine uptake. Cardiovasc. Drug Rev. 4, 369-386.

Maleddu, A., Pantaleo, M. A., Nannini, M., Di Battista, M., Saponara, M., Lolli, C. and Biasco, G. (2009). Mechanisms of secondary resistance to tyrosine kinase inhibitors in gastrointestinal stromal tumours (Review). Oncol. Rep. 6, 1359-1366.

McEwan, D. G., Brunton, V. G., Baillie, G. S., Leslie, N. R., Houslay, M. D. and Frame, M. C. (2007). Chemoresistant KM12C colon cancer cells are addicted to low cyclic AMP levels in a phosphodiesterase 4-regulated compartment via effects on phosphoinositide 3-kinase. Cancer Res. 11, 5248-5257.

Miettinen, M. and Lasota, J. (2006a). Gastrointestinal stromal tumors: pathology and prognosis at different sites. Semin. Diagn. Pathol. 2, 70-83.

Miettinen, M. and Lasota, J. (2006b). Gastrointestinal stromal tumors: review on morphology, molecular pathology, prognosis, and differential diagnosis. Arch. Pathol. Lab. Med. 10, 1466-1478.

Miettinen, M., Virolainen, M. and Maarit-Sarlomo-Rikala. (1995). Gastrointestinal stromal tumors—value of CD34 antigen in their identification and separation from true leiomyomas and schwannomas. Am. J. Surg. Pathol. 2, 207-216.

Murthy, K. S., Zhou, H. and Makhlouf, G. M. (2002). PKA-dependent activation of PDE3A and PDE4 and inhibition of adenylyl cyclase V/VI in smooth muscle. Am. J. Physiol. Cell. Physiol. 3, C508-17.

Novelli, M., Rossi, S., Rodriguez-Justo, M., Taniere, P., Seddon, B., Toffolatti, L., Sartor, C., Hogendoorn, P. C., Sciot, R., Van Glabbeke, M. et al. (2010). DOG1 and CD117 are the antibodies of choice in the diagnosis of gastrointestinal stromal tumours. Histopathology 2, 259-270.

Resjö, S., Oknianska, A., Zolnierowicz, S., Manganiello, V. and Degerman, E. (1999). Phosphorylation and activation of phosphodiesterase type 3B (PDE3B) in adipocytes in response to serine/threonine phosphatase inhibitors: deactivation of PDE3B in vitro by protein phosphatase type 2A. Biochem. J. 341, 839-845.

Seiler, S., Arnold, A. J., Grove, R. I., Fifer, C. A., Keely, S. L., Jr and Stanton, H. C. (1987). Effects of anagrelide on platelet cAMP levels, cAMP-dependent protein kinase and thrombin-induced Ca++ fluxes. J. Pharmacol. Exp. Ther. 2, 767-774.

Shakur, Y., Holst, L. S., Landstrom, T. R., Movsesian, M., Degerman, E. and Manganiello, V. (2001). Regulation and function of the cyclic nucleotide phosphodiesterase (PDE3) gene family. Prog. Nucleic Acid Res. Mol. Biol. 241-277.

Sircar, K., Hewlett, B. R., Huizinga, J. D., Chorneyko, K., Berezin, I. and Riddell, R. H. (1999). Interstitial cells of Cajal as precursors of gastrointestinal stromal tumors. Am. J. Surg. Pathol. 4, 377-389.

Snyder, E. L., Sandstrom, D. J., Law, K., Fiore, C., Sicinska, E., Brito, J., Bailey, D., Fletcher, J. A., Loda, M., Rodig, S. J., Dal Cin, P. and Fletcher, C. D. (2009). C-jun amplification and overexpression are oncogenic in liposarcoma but not always sufficient to inhibit the adipocytic differentiation programme. J. Pathol. 218, 292-300.

Tsimberidou, A. M., Colburn, D. E., Welch, M. A., Cortes, J. E., Verstovsek, S., O'Brien, S. M., Albitar, M., Kantarjian, H. M. and Giles, F. J. (2003). Anagrelide and imatinib mesylate combination therapy in patients with chronic myeloproliferative disorders. Cancer Chemother. Pharmacol. 3, 229-234.

Tuveson, D. A., Willis, N. A., Jacks, T., Griffin, J. D., Singer, S., Fletcher, C. D., Fletcher, J. A. and Demetri, G. D. (2001). STI571 inactivation of the gastrointestinal stromal tumor c-KIT oncoprotein: biological and clinical implications. Oncogene 36, 5054-5058.

Wada, T., Onogi, Y., Kimura, Y., Nakano, T., Fusanobori, H., Ishii, Y., Sasahara, M., Tsuneki, H. and Sasaoka, T. (2013). Cilostazol ameliorates systemic insulin resistance in diabetic db/db mice by suppressing chronic inflammation in adipose tissue via modulation of both adipocyte and macrophage functions. Eur. J. Pharmacol. 707, 120-129.

West R B, Corless C L, Chen X, Rubin B P, Subramanian S, Montgomery K, Zhu S, Ball C A, Nielsen T O, Patel R, Goldblum J R, Brown P O, Heinrich, M. C. and van de Rijn, M. (2004). The novel marker, DOG1, is expressed ubiquitously in gastrointestinal stromal tumors irrespective of KIT or PDGFRA mutation status. Am. J. Pathol. 165, 107-113.

Wibmer, C., Leithner, A., Zielonke, N., Sperl, M. and Windhager, R. (2010). Increasing incidence rates of soft tissue sarcomas? A population-based epidemiologic study and literature review. Ann. Oncol. 21, 1106-1111.

Yarden, Y., Kuang, W. J., Yang-Feng, T., Coussens, L., Munemitsu, S., Dull, T. J., Chen, E., Schlessinger, J., Francke, U. and Ullrich, A. (1987). Human proto-oncogene c-kit: a new cell surface receptor tyrosine kinase for an unidentified ligand. EMBO J. 11, 3341-3351.

The invention claimed is:

1. A method for treatment of gastrointestinal stromal tumor or liposarcoma in a human patient, wherein a pharmaceutically effective amount of a composition comprising anagrelide or a salt thereof is administered to a patient in need of such treatment.

2. The method according to claim 1, wherein the salt of anagrelide is anagrelide hydrochloride.

3. The method according to claim 1, wherein said composition further comprises a tyrosine kinase inhibitor.

4. The method according to claim 3, wherein said tyrosine kinase inhibitor is specific for KIT and platelet-derived growth factor receptor and is selected from the group consisting of nilotinib, sunitinib, regorafenib, imatinib, imatinib mesylate, masitinib, dovitinib, ponatinib, pazopanib, sorafenib, dasatinib, vatalanib and crenolanib.

5. The method according to claim 1, wherein said composition is administered to said patient, simultaneously or sequentially, in combination with a composition comprising a tyrosine kinase inhibitor.

6. The method according to claim 1, wherein said composition is a pharmaceutical composition comprising pharmaceutically acceptable buffer, carrier or adjuvant.

7. The method according to claim 6, wherein said pharmaceutical composition is formulated for sustained-release, delayed-release, or timed-release, or said pharmaceutical composition is a blend of sustained-release and immediate-release formulations.

* * * * *

SEQUENCE LISTING

```
<160> NUMBER OF SEQ ID NOS: 8

<210> SEQ ID NO 1
<211> LENGTH: 23
<212> TYPE: DNA
<213> ORGANISM: Artificial sequence
<220> FEATURE:
<223> OTHER INFORMATION: Oligonucleotide primer

<400> SEQUENCE: 1
aaagacaagc ttgctattcc aaa                                              23

<210> SEQ ID NO 2
<211> LENGTH: 22
<212> TYPE: DNA
<213> ORGANISM: Artificial sequence
<220> FEATURE:
<223> OTHER INFORMATION: Oligonucleotide primer

<400> SEQUENCE: 2
gtggaagaaa ctcgtctcaa ca                                               22

<210> SEQ ID NO 3
<211> LENGTH: 24
<212> TYPE: DNA
<213> ORGANISM: Artificial sequence
<220> FEATURE:
<223> OTHER INFORMATION: Oligonucleotide primer

<400> SEQUENCE: 3
tgaatcttgg ttgtaaactt gacc                                             24

<210> SEQ ID NO 4
<211> LENGTH: 20
<212> TYPE: DNA
```

```
<213> ORGANISM: Artificial sequence
<220> FEATURE:
<223> OTHER INFORMATION: Oligonucleotide primer

<400> SEQUENCE: 4
ctcatgatta ccgcagcaaa                                            20

<210> SEQ ID NO 5
<211> LENGTH: 26
<212> TYPE: DNA
<213> ORGANISM: Artificial sequence
<220> FEATURE:
<223> OTHER INFORMATION: Oligonucleotide primer

<400> SEQUENCE: 5
aacaatggta taagcctcat tatcaa                                     26

<210> SEQ ID NO 6
<211> LENGTH: 20
<212> TYPE: DNA
<213> ORGANISM: Artificial sequence
<220> FEATURE:
<223> OTHER INFORMATION: Oligonucleotide primer

<400> SEQUENCE: 6
cgagcctcat ttagcactga                                            20

<210> SEQ ID NO 7
<211> LENGTH: 19
<212> TYPE: DNA
<213> ORGANISM: Artificial sequence
<220> FEATURE:
<223> OTHER INFORMATION: Oligonucleotide primer

<400> SEQUENCE: 7
gagccagatg cacttcgtg                                             19

<210> SEQ ID NO 8
<211> LENGTH: 19
<212> TYPE: DNA
<213> ORGANISM: Artificial sequence
<220> FEATURE:
<223> OTHER INFORMATION: Oligonucleotide primer

<400> SEQUENCE: 8
gggcttctcc agctcaatc                                             19
```